United States Patent [19]

Hovel, III

[11] Patent Number: 4,712,572

[45] Date of Patent: Dec. 15, 1987

[54] DENTAL FLOSS PACKET AND METHOD FOR ITS MANUFACTURE

[76] Inventor: William G. Hovel, III, P.O. Box 26766, El Paso, Tex. 79926

[21] Appl. No.: 907,991

[22] Filed: Sep. 16, 1986

[51] Int. Cl.$^4$ ............................................... A61C 7/00
[52] U.S. Cl. ...................................... 132/89; 132/93; 206/581
[58] Field of Search ................... 132/89 A, 89, 90, 91, 132/92 R, 92 A; 206/581; 433/141

[56] References Cited

U.S. PATENT DOCUMENTS 4,105,120  8/1978  Bradberry ...................... 132/92 R
4,633,892  6/1987  Charatan .............................. 132/93

Primary Examiner—Robert Peshock
Attorney, Agent, or Firm—Richard C. Litman

[57] ABSTRACT

A dental floss packet consisting of a first water resistant sheet of material having a determined configuration with a left periphery and a right periphery, a length of dental floss having one end thereof secured to a portion of the left periphery of the material and having another end thereof secured to a portion of the right periphery thereof, a second water resistant sheet of the material having a similar configuration as the first sheet of material, a die stamped seal extending entirely along the periphery between the sheets of the material and enclosing therewithin the dental floss, and indicating a tear strip for extending transverse to the composite sheet assembly and intermediate the left periphery of the material and the right periphery thereof.

6 Claims, 2 Drawing Figures

DENTAL FLOSS PACKET AND METHOD FOR ITS MANUFACTURE

BACKGROUND OF THE INVENTION

1. Field of the Invention

The invention relates to a dental floss packet and its method for manufacture, and more particularly the invention is directed to a dental floss package consisting of a first water resistant sheet of material having a determined configuration with a left periphery and a right periphery, a length of dental floss having one end thereof secured to a portion of the left periphery of the material and having the other end thereof secured to a portion of the right periphery thereof, a second water resistant sheet of the material having a similar configuration as the first sheet of material, a stamped seal extending entirely along the periphery between the sheets of material and enclosing therewithin the dental floss, and indicating a tear strip extending transverse to the composite sheet assembly and intermediate the left periphery of the material and the right periphery thereof.

The invention relates further to a device providing for manufacture of a dental floss packet consisting of cutting and forming a first water resistant sheet of material having a determined configuration with a left periphery and a right periphery, inserting a length of dental floss having one end thereof secured to a portion of the left periphery of the material and having another end thereof secured to a portion of the right periphery, cutting and forming a second water resistant sheet of the material having a similar configuration as the first sheet of material, die stamping and sealing the sheets of material together along the entire periphery between the sheets of material and for enclosing therewithin the dental floss, and indicating a tear strip for extending transverse to the composite sheet assembly and intermediate the left periphery of the material and the right periphery thereof as more particularly described herein.

Flossing between the teeth has for a considerable amount of time been highly recommended by the dental profession, however, most persons may find it at times inconvenient to carry a normal package or roll of dental floss with them during the day and hence do not floss after mid-day or away from home meals. The invention describes and proposes to resolve the problem by placing an individual strand of dental floss within a water proof package which could easily be carried in the shirt pocket, wallet or purse of an individual. Further, such individual packages of dental floss could be used by persons in the dental fields as promotional and advertising items which would be extremely beneficial to the recipient of the packet of the invention.

The invention seeks to provide a packet and by the teaching of steps of its manufacture a package comprised of paper or Cellophane ® so as to be impervious to water, the packet being cut and formed in the shape of a molar and sealed at the edges to prevent the entrance of water or other contaminant and to clasp firmly the ends of approximately 18 inches of dental floss at each side. The shape of the package would further allow the printing of any advertising or identification directly onto the package. In use an individual would simply tear the paper or material of the package down a mid-section or the middle of the package and draw out the dental floss contained therein. Each side of the package would then serve as a convenient handle to aid the grasping of the ends of the dental floss during its use.

2. Description of the Prior Art

Various prior art medical and dental package devices, and the like, as well as apparatus and method of their construction in general are found to be known, and exemplary of the U.S. prior art are the following:

| | |
|---|---|
| 2,083,398 | C. J. Rohland |
| 2,443,415 | J. Buscarino |
| 2,981,264 | A. F. De Felice |
| 3,696,821 | John Q. Adams, IV |
| 3,744,499 | R. L. Wells |
| 3,901,251 | J. A. Johnston |
| 4,315,517 | M. D. Krag |

The patents or known prior uses teach and disclose various types of dental floss packages and devices of sorts and of various manufactures and the like as well as methods of their construction, but none of them whether taken singly or in combination disclose the specific details of the combination of the invention in such a way as to bear upon the claims of the present invention.

SUMMARY OF THE INVENTION

An object, advantage and feature of the invention is to provide a novel dental floss packet that will allow the recipient to carry it with him or her and use it for away from home meals.

Another object of the invention is directed to a device providing for a construction of a dental floss packet conveniently sized and shaped to allow printing on one or each side providing any information for its use, including a company or manufacturer's logo, oral hygiene instructions for its use and disposition, and any message a distributor of a dental floss packet may desire to choose, and thus to maximize the beneficial effects of the device to both the recipient as an oral hygiene aid and to the distributor as a promotional or educational tool.

Also an object of the invention is to provide a simple and direct method for improved construction of a dental floss packet that is easy to store and carry as well as to use.

Another object of the invention is to provide a dental floss packet composed of Cellophane ®, foil, a water resistant paper or a plastic coated paper similar to the water resistant paper used in medical packets such as an Anacin ® packet. The dental floss may be shaped as a molar or the like and will also be die stamped and sealed along the entire periphery with each end of the dental floss fixed within the sealed border on each right and left sides. This seal creates the waterproofness to insure sterility of the enclosed dental floss.

These together with other objects and advantages which will become subsequently apparent reside in the details of the process and operation thereof as more fully hereinafter is described and claimed, reference being had to the accompanying drawings forming a part hereof, wherein like numerals refer to like parts throughout.

DESCRIPTION OF A PREFERRED EMBODIMENT OF THE INVENTION

Figure 1:
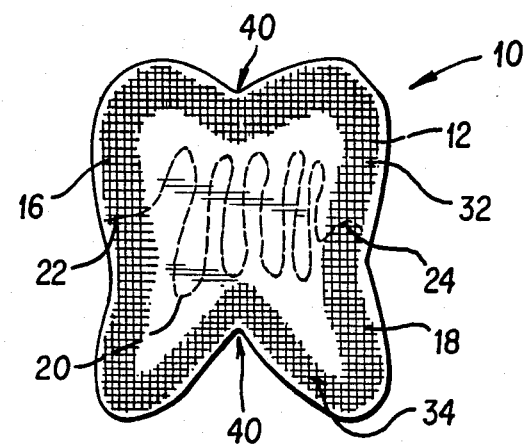
FIG. 1 is plan view of a dental floss packet and illustrating a typical construction of the dental floss packet according to a preferred embodiment and best mode of the present invention.

Referring now to the drawings there is shown in the figures a dental floss packet 10 constructed of a rear, or backing member defined as a first water resistant sheet 12 of material having a determined configuration with a left periphery 16 and a right periphery 18, a length of dental floss 20 having one end 22 secured to a portion of the left periphery 16 of the material and having another end 24 secured to a portion of the right periphery 18. A front and second water resistant sheet 32 of the material has a similar configuration as the first sheet 12 of material and a stamped seal portion 34 extends entirely along the periphery 16, 18 between the sheets 12, 32 of material and encloses therewithin the dental floss 20. The resultant packet 10 will be seen to be suggestive of a molar wherein a bi-lobal construction is presented having a top or coronal periphery 33 including an elevated left peak 35 laterally spaced from an elevated right peak 36 with an intermediate apex 40, forming a noticeable depression or valley. The bi-lobal construction is carried out by a bottom periphery 37 defining a furcation comprising a depending left root 38 laterally spaced from a depending right root 39 and including an intermediate apex or indentation 40'.

Figure 2:
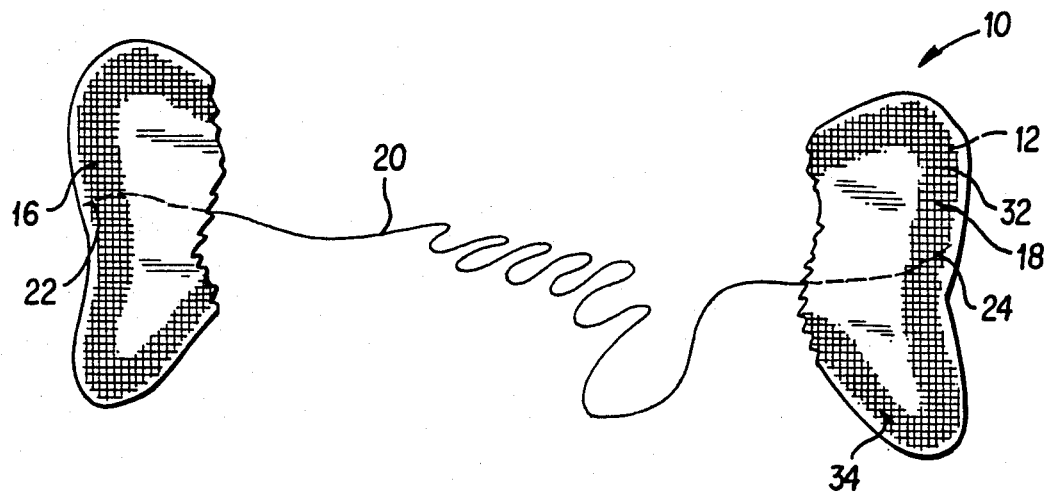
FIG. 2 is a plan view of the dental floss packet after it has been torn and opened for use according to the practice of the invention.

With the above construction in mind it will be appreciated that the resultant imaginary line or axis joining the top and bottom apices 40, 40' substantially bisects the left and right peripheries of the molar configuration. This arrangement serves to permit ready separation of the packet left and right portions along the above axis as a user grasps the two portions and tears the joined front and rear sheets 32,12 from one apex 40 to the other apex 40' or vice versa. Following this separation, the packet will appear as in FIG. 2 wherein the two portions 16 and 18 will be seen to have respective ends 22, 24 of the dental floss 20 anchored thereto so that the packet halves serve as handles during use of the span of dental floss 20. The material of the sheets 12, 32 may be of paper, Cellophane ®, a foil of metal or a foil coated paper, or water resistant paper such as plastic coated paper.

The manufacture of the dental floss packet 10 consists of steps of cutting and forming the first water resistant sheet 12 of material having a determined configuration with a left periphery 16 and a right periphery 18; inserting a length of dental floss having one end 22 secured to a portion of the left periphery 16 of the material and having the other end 24 secured to a portion of the right periphery 18; then cutting and forming a second water resistant sheet 32 of the material having a similar configuration as the first sheet 12 of material; die stamping along the periphery 16, 18 with a sealant the sheets 12, 32 of material together along the entire periphery 16, 18 between the sheets 12, 32 of material and enclosing therewithin the dental floss 20; and indicating, either by printed indicia provided on the sheets 12, 32 or from the configuration of the packet 10, a tear portion or strip 40 for extending transversely to the composite sheet assembly.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to falling within the scope of the invention.

What is claimed and desired to be secured by Letters Patent is:

1. A dental floss packet comprising;
   first and second overlying sheets of water resistant material defining a bi-lobal configuration representative of a molar, said overlying sheets having a left and right periphery,
   said packet including a top periphery having elevated left and right peaks and an intermediate depression forming a top apex, a bottom periphery having depending left and right roots and an intermediate indentation forming a bottom apex,
   a length of dental floss between said sheets having one end thereof secured to a portion of said left periphery and having another end thereof secured to a portion of said right periphery,
   a die stamped seal extending entirely along said peripheries to secure said sheets together with said dental floss therebetween, and
   an axis between said two apices substantially bisects said packet and defines a dimension representing the minimum distance between said top and bottom peripheries whereby,
   a path of least resistance is presented by said apices as said left and right peripheries are grasped to tear apart said overlying sheets along the line between said apices.
2. The apparatus of claim 1 wherein the material is paper.
3. The apparatus of claim 1 wherein the material is cellophane ®.
4. The apparatus of claim 1 wherein the material is foil.
5. The apparatus of claim 1 wherein the material is plastic coated paper.
6. The apparatus of claim 1 wherein the seal provides adequate waterproofness to insure sterility of the enclosed dental floss.

* * * * *